United States Patent
Raulerson et al.

(10) Patent No.: US 7,413,561 B2
(45) Date of Patent: Aug. 19, 2008

(54) CONDUIT RETAINING CLIP

(75) Inventors: J. Daniel Raulerson, Brewton, AL (US); Kenneth W. Aldridge, Tuscaloosa, AL (US); Mark S. Fisher, Sellersville, PA (US); William Shaun Wall, North Wales, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 10/909,554

(22) Filed: Aug. 2, 2004

(65) Prior Publication Data

US 2005/0038453 A1 Feb. 17, 2005

Related U.S. Application Data

(60) Provisional application No. 60/494,820, filed on Aug. 13, 2003.

(51) Int. Cl.
*A61M 5/32* (2006.01)
(52) U.S. Cl. ..................................... 604/174
(58) Field of Classification Search ......... 604/174–180; 128/DIG. 6, DIG. 26
See application file for complete search history.

(56) References Cited

U.S. PATENT DOCUMENTS

| 4,397,647 | A | * | 8/1983 | Gordon | 604/180 |
|---|---|---|---|---|---|
| 4,645,492 | A | | 2/1987 | Weeks | |
| 4,650,474 | A | | 3/1987 | De Backer | |
| 4,699,616 | A | * | 10/1987 | Nowak et al. | 604/180 |
| 4,711,636 | A | | 12/1987 | Bierman | |
| 4,981,475 | A | | 1/1991 | Haindl | |
| 4,997,421 | A | | 3/1991 | Palsrok et al. | |
| 5,069,206 | A | * | 12/1991 | Crosbie | 128/207.17 |
| 5,192,273 | A | | 3/1993 | Bierman | |
| 5,224,935 | A | | 7/1993 | Hollands | |
| 5,290,248 | A | | 3/1994 | Bierman et al. | |
| D347,060 | S | | 5/1994 | Bierman | |
| 5,314,411 | A | | 5/1994 | Bierman et al. | |
| 5,318,546 | A | | 6/1994 | Bierman | |
| 5,354,282 | A | | 10/1994 | Bierman | |
| 5,370,624 | A | | 12/1994 | Edwards et al. | |
| 5,456,671 | A | | 10/1995 | Bierman | |
| D364,922 | S | | 12/1995 | Bierman | |
| 5,509,902 | A | * | 4/1996 | Raulerson | 604/175 |
| D375,355 | S | | 11/1996 | Bierman | |

(Continued)

*Primary Examiner*—LoAn H. Thanh
(74) *Attorney, Agent, or Firm*—Anton P. Ness; Fox Rothschild LLP

(57) ABSTRACT

A clip (100) for releasably retaining a conduit (140) including a first base portion (102), a second base portion (104), and a hinge (106) connecting the first base portion to the second base portion. A generally arcuate first connector portion (110) has a first connected end (112) extending from the first base portion and a first free end (114). The first free end includes a first tabbed extension (116) and a first locking portion (118) adjacent to the first tabbed extension. A generally arcuate second connector portion (120) has a second connected end (122) extending from the second base portion and a second free end (124). The second free end includes a second tabbed extension (126) and a second locking portion (128) adjacent to the second tabbed extension. The first connector portion (110) and the second connector portion (120) are juxtaposed from each other across the hinge (106). The first tabbed extension (116) is releasably engageable with the second locking portion (128) and the second tabbed extension (126) is releasably engageable with the first locking portion (118).

18 Claims, 3 Drawing Sheets

U.S. PATENT DOCUMENTS

| | | | |
|---|---|---|---|
| D375,356 S | 11/1996 | Bierman | |
| 5,578,013 A | 11/1996 | Bierman | |
| 5,637,098 A | 6/1997 | Bierman | |
| 5,702,371 A | 12/1997 | Bierman | |
| 5,755,225 A * | 5/1998 | Hutson | 128/207.18 |
| 5,800,402 A | 9/1998 | Bierman | |
| 5,810,781 A | 9/1998 | Bierman | |
| 5,827,230 A | 10/1998 | Bierman | |
| 5,833,667 A | 11/1998 | Bierman | |
| 5,947,931 A | 9/1999 | Bierman | |
| 6,132,398 A | 10/2000 | Bierman | |
| 6,213,979 B1 | 4/2001 | Bierman | |
| 6,224,571 B1 | 5/2001 | Bierman | |
| 6,290,676 B1 | 9/2001 | Bierman | |
| 6,428,515 B1 | 8/2002 | Bierman et al. | |
| 6,428,516 B1 | 8/2002 | Bierman | |
| 6,447,485 B2 | 9/2002 | Bierman | |
| 6,491,664 B2 | 12/2002 | Bierman | |
| 6,572,588 B1 | 6/2003 | Bierman | |
| 7,070,579 B1 | 7/2006 | Harper | |

* cited by examiner

CONDUIT RETAINING CLIP

The present application claims priority from U.S. Provisional Patent Application Ser. No. 60/494,820, filed on 13 Aug. 2003.

BACKGROUND OF THE INVENTION

Field of the Invention

The present invention relates to a clip that is used to retain a conduit, such as a catheter, in a fixed position.

BACKGROUND OF THE INVENTION

Catheters are often used to administer fluid or to withdraw fluid from a body of a patient. The catheters may be inserted into the patient's body for a short period of time, such as for a few hours or day, or for extended periods of time, such as weeks or months. Some examples of catheters are urinary catheters, hemodialysis catheters, and peripherally inserted central catheters (PICCs). A distal portion of the catheter is inserted into the patient, while a proximal portion of the catheter extends exterior of the patient.

However, the proximal portion of the catheter tends to dangle from the insertion location into the patient and is susceptible to snagging or accidental dislodging from the insertion location. Medical personnel typically use surgical or other adhesive tape to secure the proximal portion of the catheter to the patient's skin in order to reduce movement of the catheter relative to the patient, and to reduce the risk of accidental catheter dislodgement. However, the frequent application and removal of the tape, such as to clean and disinfect the area proximate the insertion location of the catheter and underneath the catheter, may be very discomforting to the patient.

Catheter securing devices have been developed that secure part of the proximal portion of the catheter to the exterior skin of the patient in order to eliminate the need for the use of tape as described above. Examples of such devices are shown in U.S. Pat. Nos. 5,637,098; 6,213,979; and 6,447,485. However, these devices are either single use applications or fairly complex devices that require several steps and a fairly significant amount of time to secure the catheter to the device. It would be beneficial to provide a catheter securing device that may be used multiple times, yet is sufficiently simple to use that it does not take much time for the medical personnel to properly and securely retain the catheter to the patient.

BRIEF SUMMARY OF THE INVENTION

Briefly, the present invention provides a retaining clip for a conduit. The clip comprises a first base portion, a second base portion, and a hinge connecting the first base portion to the second base portion. A generally arcuate first connector portion has a first connected end extending from the first base portion and a first free end. The first free end includes a first tabbed extension and a first locking portion adjacent to the first tabbed extension. A generally arcuate second connector portion has a second connected end extending from the second base portion and a second free end. The second free end includes a second tabbed extension and a second locking portion adjacent to the second tabbed extension. The first connector portion and the second connector portion are juxtaposed from each other across the hinge. The first tabbed extension is releasably engageable with the second locking portion and the second tabbed extension is releasably engageable with the first locking portion.

Further, the present invention provides a retainer clip comprising a first body portion extending generally along a first side of a plane, a second body portion extending generally along a second side of the plane, and a hinge member connecting the first body portion and the second body portion. The hinge member extends along the plane. The clip also includes a locking section for releasably connecting the first body portion and the second body portion and means for releasably connecting the retainer clip to a surface.

BRIEF DESCRIPTION OF THE DRAWINGS

The accompanying drawings, which are incorporated herein and constitute part of this specification, illustrate the presently preferred embodiment of the invention, and, together with the general description given above and the detailed description given below, serve to explain the features of the invention. In the drawings.

DETAILED DESCRIPTION OF THE INVENTION

Figure 1:
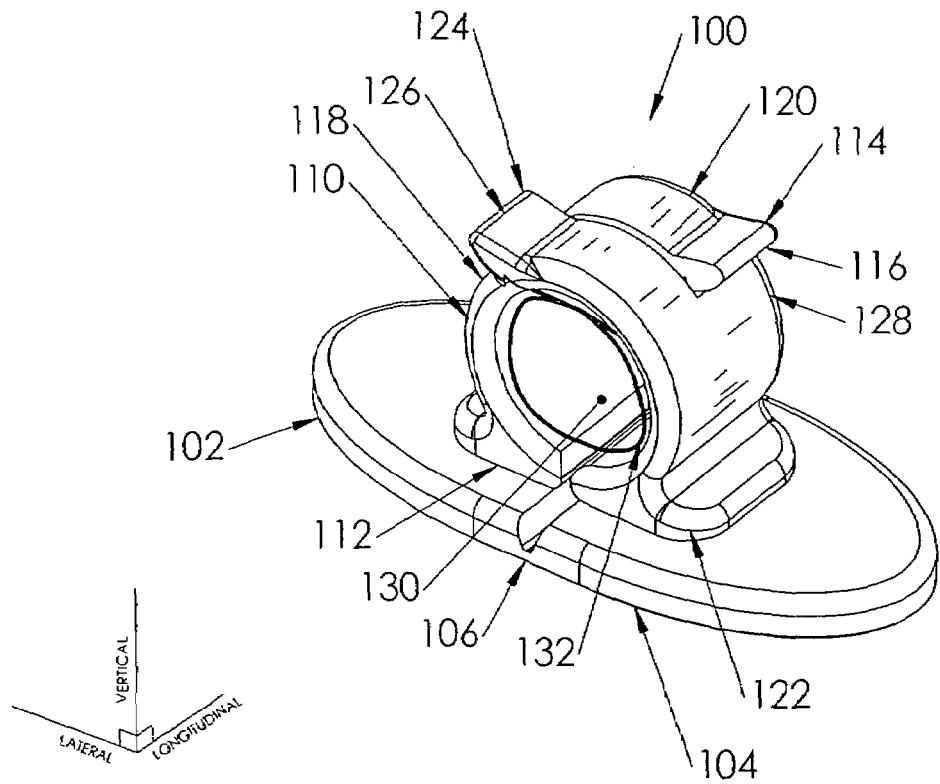
FIG. 1 is a perspective view of a conduit retaining clip according to a preferred embodiment of the present invention.

In the drawings, like numerals indicate like elements throughout. Certain terminology is used herein for convenience only and is not to be taken as a limitation on the present invention. The terminology includes the words above specifically mentioned, derivatives thereof, and words of similar import. The following describes a preferred embodiment of the invention. However, it should be understood based on this disclosure, that the invention is not limited by the preferred embodiment described herein.

Referring now to the drawings in detail, there is shown in FIG. 1 a perspective view of a conduit retaining clip 100 according to a preferred embodiment of the present invention. The clip 100 may be used to retain a conduit, such as a catheter or other fluid transporting device against a fixed location, such as the external skin of a patient. The conduit may be a single catheter or a plurality of catheters, such as in a multi-lumen catheter assembly. Alternatively, those skilled in the art will recognize that the clip 100 may be used to retain other generally tubular devices, such as electrical cabling or wiring.

Figure 2:
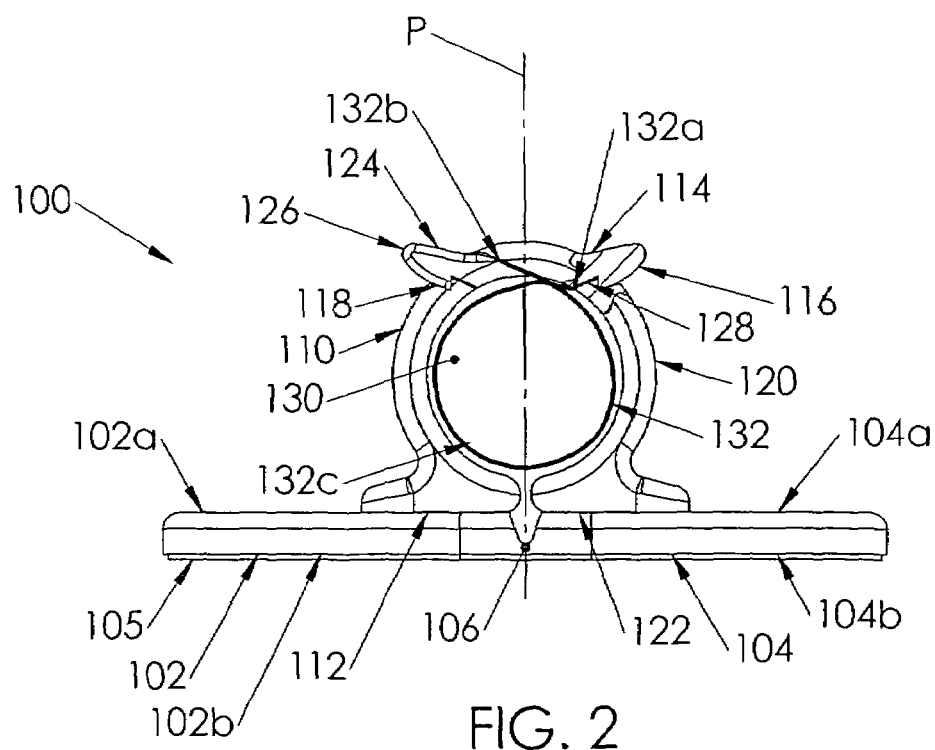
FIG. 2 is a side elevation view, partially broken away, of the conduit retaining clip of FIG. 1.

Referring to FIG. 2, the clip 100 includes a first base portion 102 and a second base portion 104. Each of the first and second base portions 102, 104 includes a top face 102a, 104a and a bottom face 102b, 104b, respectively. Each bottom face 102b, 104b is disposed away from each respective top face 102a, 104a. A total length of the first base portion and the second base portion is preferably between approximately 5 and 7 centimeters, although the length may be varied according to the size of the conduit that is to be disposed within the clip 100.

The bottom face 102b, 104b of each of the first and second base portions 102, 104, respectively, preferably includes an adhesive 105 to affix the clip 100 to a surface, such as the exterior skin surface of a patient. The adhesive 105 used to retain the clip 100 is preferably strong enough to retain the clip 100 to the patient's skin but weak enough so that the clip 100 may be removed from the patient's skin without tearing or ripping the skin.

Figure 3:
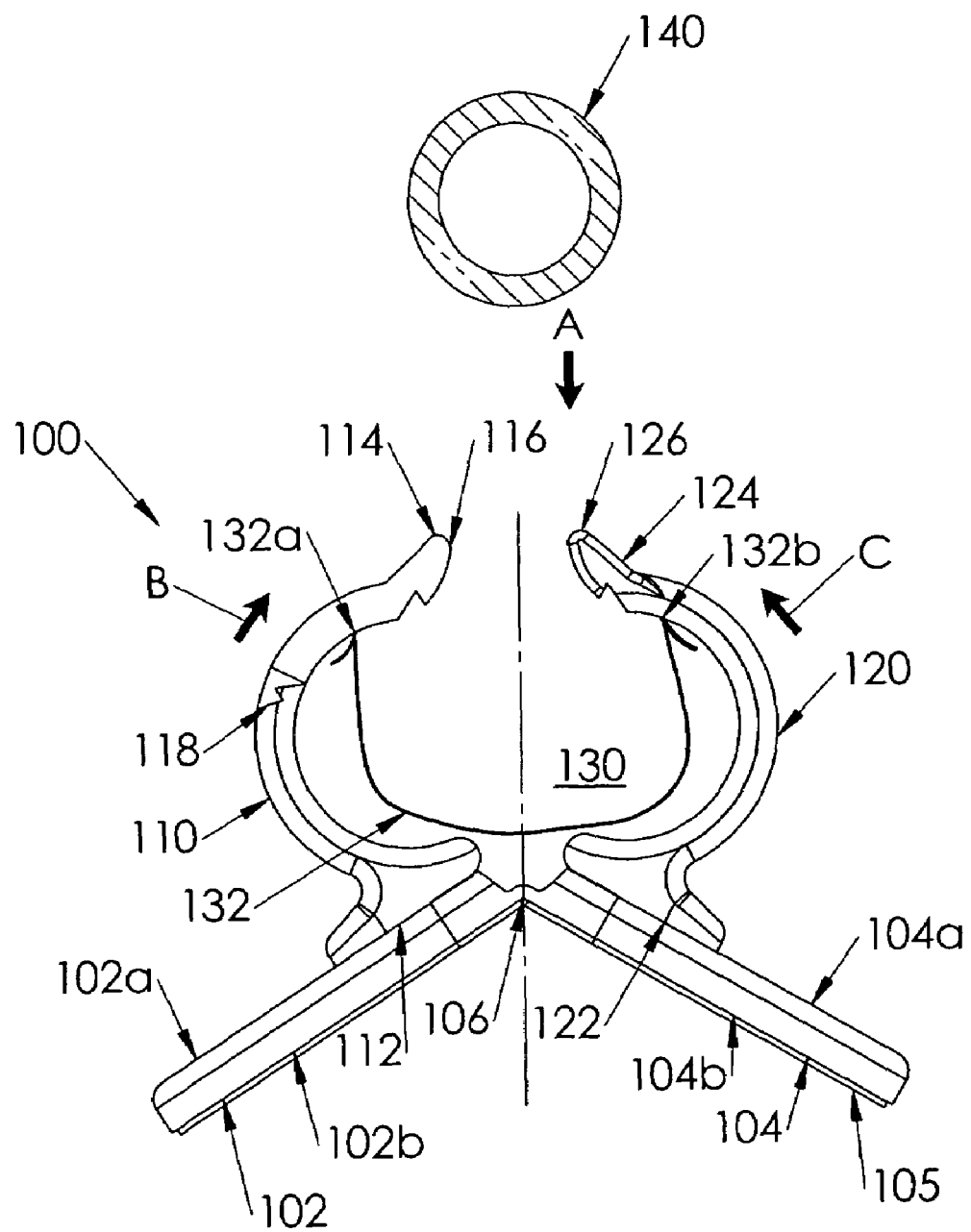
FIG. 3 is a side elevation view of the conduit retaining clip of FIG. 1 in an open position, with a conduit being inserted therein.

The first and second base portions 102, 104 are connected to each other by a hinge 106. The type of hinge 106 provided is not critical to the operation of the clip 100. While the hinge 106 shown is a preferred living hinge 106, those skilled in the art will recognize that other types of hinges may be used to connect the first base portion 102 and the second base portion 104. The hinge 106 is disposed to allow the first and second bottom faces 102b, 104b to be disposed toward each other, as shown in FIG. 3.

Referring back to FIGS. 1 and 2, a generally arcuate first connector portion 110 includes a first connected end 112 that is fixedly connected to and extends from the top face 102a of the first base portion 102. The first connector portion 110 also includes a first free end 114 that includes a first tabbed extension 116 and a first locking portion 118 adjacent to the first tabbed extension 116. The first tabbed extension 116 extends in an approximately 220 degree arc from the first base portion 102. The first locking portion 118 extends in an approximately 140 degree arc from the first base portion 102.

A generally arcuate second connector portion 120, includes a second connected end 122 that is fixedly connected to and extends from top face 104a of the second base portion 104. The second connector portion 120 also includes a second free end 124 that includes a second tabbed extension 126 and a second locking portion 128 adjacent to the second tabbed extension 126. The second tabbed extension 126 extends in an approximately 220 degree arc from the second base portion 104. The second locking portion 128 extends in an approximately 140 degree arc from the second base portion 104.

The first connector portion 110 and the second connector portion 120 are preferably generally identical to each other, but are juxtaposed from each other across the hinge 106 such that the first tabbed extension 116 is releasably engageable with the second locking portion 128 and the second tabbed extension 126 is releasably engageable with the first locking portion 118, defining a locking section of clip 100.

A plane "P" bisects the clip 100 through the hinge 106 such that, when the clip 100 is in the closed position, the first tabbed extension 116 is on an opposing side of the plane P from a remainder of the first connector portion 110. The second tabbed extension 126 is on the same side of the plane P as the remainder of the first connector portion 110 and the remainder of the second connector portion 120 is on the same side of the plane P as the first tabbed extension 116.

When the clip 100 is in a closed position, a generally circular passageway 130 is defined through the clip 100. The passageway 130 is sized to allow a conduit 140, shown in FIG. 3, to be inserted longitudinally therein. Referring back to FIG. 2, a flexible member, such as a thread 132, extends into the passageway 130. Such a flexible member is disclosed in the catheter stabilizing device of U.S. Pat. No. 5,509,902. A first end 132a of the thread 132 is fixedly connected to the first tabbed extension 116 and a second end 132b of the thread 132 is fixedly connected to the second tabbed extension 126. A thread body 132c extends between the first end 132a and the second end 132b. The thread 132 preferably hangs in the passageway 130 in a generally U-shaped fashion, as shown in FIG. 3, and in an overlapping fashion as shown in FIGS. 1 and 2 when the connector portions 110, 120 are closed and locked to each other. The thread 132 may be surgical suture, silk, nylon, or some other suitable material. The purpose of the thread 132 is to helically loop around the conduit 140 to retain the conduit 140 within the passageway 130 when the clip 100 is in the closed position. The loop forms greater than 360 degree circumference about conduit 124 when the clip is in the closed state, and then is tight enough to restrict longitudinal translation of the conduit 140 along the passageway 130, but not tight enough as to restrict fluid flow through the conduit 140. In the event that the conduit 140 is attempted to be translated longitudinally the thread 132 grasps the conduit 140 even more tightly to restrict such translation.

Preferably, the clip 100 is constructed from a polymer, and more preferably, from polypropylene, although those skilled in the art will recognize that other, suitable material may be used. The clip 100 may be of unitary construction, with the thread 132 fixed to the first and second tabbed extensions 116, 126 after the clip 100 is manufactured, or alternatively, the clip 100 may be constructed in several pieces, such as separate first and second connector portions 110, 120 that are separately bonded to the first and second base portions 102, 104, respectively. The first and second connector portions 110, 120 may be bonded to the first and second base portions 102, 104 by adhesive bonding, ultrasonic bonding, or any other suitable bonding method known to those skilled in the art.

Use of the clip 100 in a preferred manner will now be described. A location for fixation of the clip 100 is determined on the skin of the patient. The location may be determined before or after inserting or connecting the conduit 140 that is to be retained by the clip 100. Preferably, the surface of the skin is shaved or otherwise prepared to remove extraneous hair from the skin so as to not rip hair or otherwise cause pain to the patient when the clip 100 is eventually removed from the patient. A backing material (not shown) that may be affixed over the adhesive 105 on each of the bottom faces 102b, 104b of the first and second base portions 102, 104, respectively, is removed, exposing the adhesive 105. The clip 100 is opened by pivoting the first and second connector portions 110, 120 about the hinge 106 to the position shown in FIG. 3. The first tabbed extension 116 is on the same side of the plane P as the first base portion 102 and the second tabbed extension 126 is on the same side of the plane P as the second base portion 104.

The conduit 140 is then disposed between the first and second tabbed extensions 116, 126, respectively, along arrow "A" of FIG. 3 and into the now opened passageway 130. After the conduit 140 has cleared the first and second tabbed extensions 116, 126, the clip 100 is closed by pivoting the first and second connector portions 110, 120 about the hinge 106 in the direction of arrows "B" and "C", respectively, so that the first tabbed extension 116 releasably engages the second locking portion 128 and the second tabbed extension 126 releasably engages the first locking portion 118.

As the first and second connector portions 110, 120 are pivoted about the hinge 106, the first tabbed extension 116 is moved to the same side of the plane P as the second base portion 104 and the second tabbed extension 126 is moved to the same side of the plane P as the first base portion 102. The first tabbed extension 116 snaps into the second locking portion 128, releasably locking the first tabbed extension 116 to the second locking portion 128. The second tabbed extension 126 snaps into the first locking portion 118, releasably locking the second tabbed extension 126 to the first locking portion 118.

Figure 4:
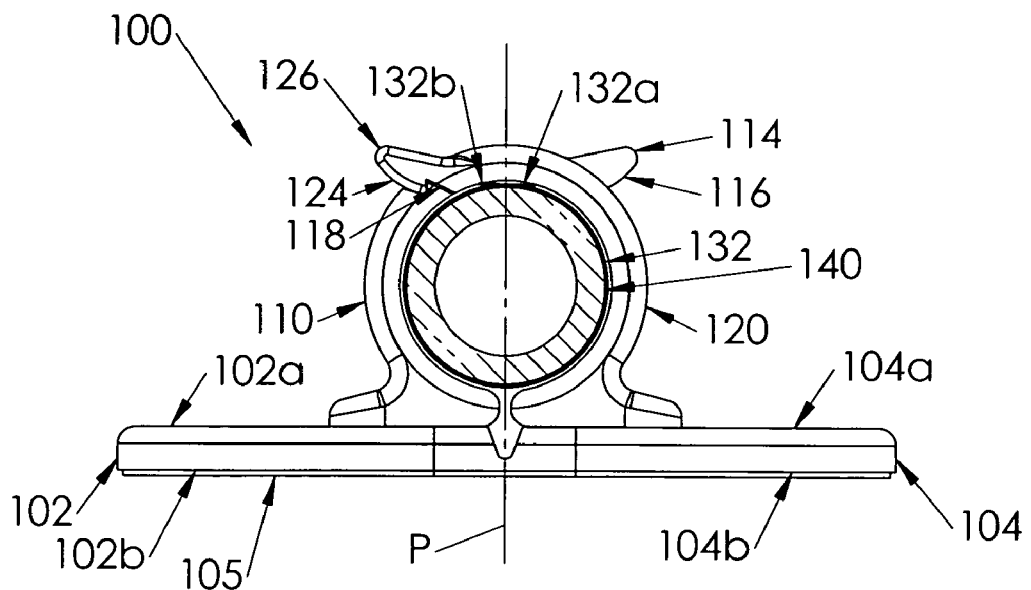
FIG. 4 is a side elevation view of the conduit retaining clip of FIG. 3, with the conduit having been inserted therein.
Figure 5:
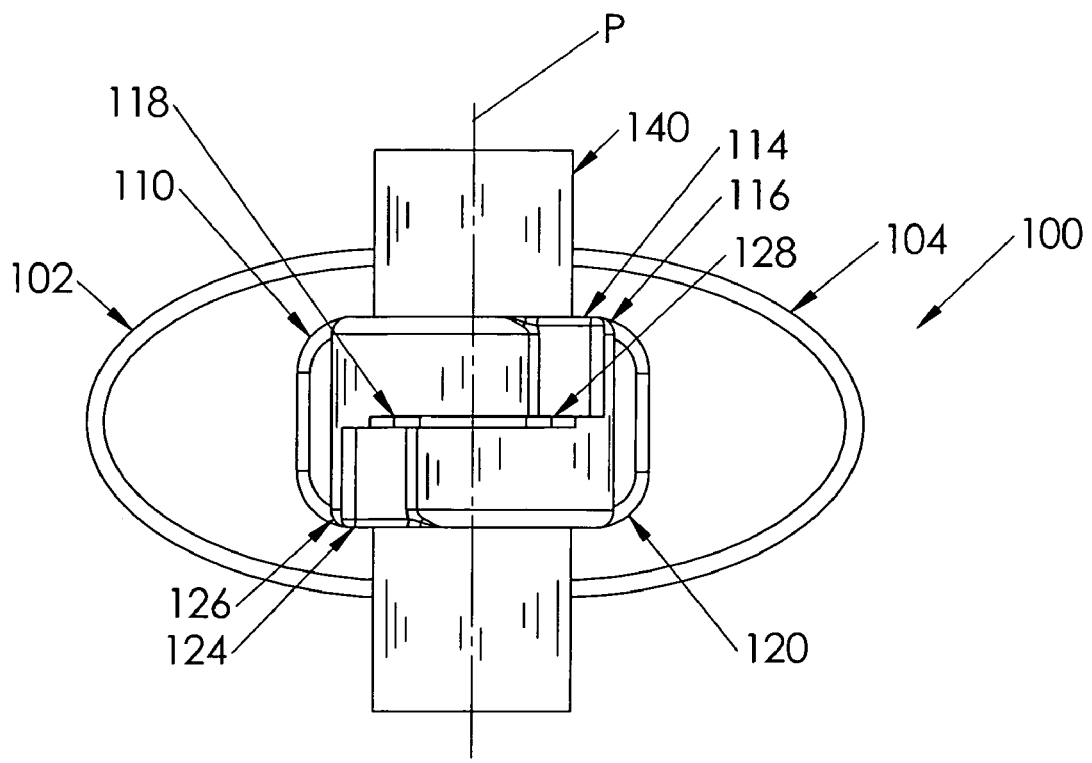
FIG. 5 is a top plan view of the conduit retaining clip of FIG. 3, with the conduit having been inserted therein.

The first and second ends 132a, 132b of the thread 132 loop around the conduit 140 in a generally helical fashion so that the thread 132 engages the conduit 140 over an arc of more than 360 degrees, as shown in FIG. 4. The conduit 140 is now frictionally retained within the clip 100 by the thread 132. If the conduit 140 is attempted to be longitudinally translated (ie. out of the page of FIG. 4 or top-to-bottom of the page of FIG. 5, the thread 132 tightens around the conduit 140, restraining movement of the conduit 140.

To open the clip 100 and release the conduit 140 from the clip 100, the first free end 114 and the second free end 124 are both biased away from the second and first base portions 104, 102, respectively, and toward the plane P. The first tabbed extension 116 releases from the second locking portion 128 and the second tabbed extension 126 releases from the first locking portion 118, allowing the hinge 106 to pivot the first and second connector portions 110, 120, respectively, away from the plane P. The first and second ends 132a, 132b of the thread 132 separate away from the conduit 140, releasing the conduit 140 from the thread 132. The conduit 140 may be removed from the clip 100 by lifting the conduit 140 along the plane P between the first and second connector portions 110, 120.

While a preferred use of the clip 100 to retain a conduit 140, such as a catheter, to a surface, such as a patient's skin, has been described, those skilled in the art will recognize that the clip 100 is not restricted to the use described, but may be used to retain any type of generally elongated body generally longitudinally with respect to the clip 100, on any type of a surface that will accommodate the clip 100.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A retaining clip for a conduit comprising:
   a base having a first base portion, a second base portion, and a hinge connecting the first base portion to the second base portion; and
   a conduit-containing portion having first and second connector portions for defining therebetween a passage for a conduit, wherein
   the first connector portion is generally arcuate having a first connected end extending from the first base portion and a first free end, wherein the first free end includes a first tabbed extension and a first locking portion adjacent to the first tabbed extension; and
   the second connector portion is generally arcuate having a second connected end extending from the second base portion and a second free end, wherein the second free end includes a second tabbed extension and a second locking portion adjacent to the second tabbed extension, wherein the first connector portion and the second connector portion are juxtaposed from each other across the hinge, and wherein the first tabbed extension is releasably engageable with the second locking portion and the second tabbed extension is releasably engageable with the first locking portion to define the passage for the conduit.

2. The retaining clip according to claim 1, further comprising a flexible member having a first end connected to the first tabbed extension, and a second end connected to the second tabbed extension, and a body between the first end and the second end extending generally between the first and second connected ends that has a length greater than the circumference of the conduit to be placed into the conduit-containing portion.

3. The retaining clip according to claim 2, wherein the flexible member comprises a thread.

4. The retaining clip according to claim 1, wherein the first and second base portions each comprise a first and second bottom side, respectively, wherein each of the first and second bottom sides are disposed away from each of the first and second base portions, respectively.

5. The retaining clip according to claim 4, wherein each bottom side comprises an adhesive for adherence of the retaining clip to a surface.

6. The retaining clip according to claim 4, wherein the hinge is disposed to allow the first and second bottom sides to be disposed toward each other when the first and second connector portions are disengaged from each other to release a conduit held in the passage.

7. The retainer clip according to claim 1 further comprising a plane extending through the hinge generally perpendicular to the first and second base portions when the retainer clip is in a closed position, wherein, when the retainer clip is in the closed position, the first free end is on a first side of the plane and the second free end is on a second side of the plane and, wherein, when the retainer clip is in an open position, the first free end is on the second side of the plane and the second free end is on the first side of the plane.

8. The retainer clip according to claim 1, wherein the retainer clip is constructed from a polymer.

9. The retainer clip according to claim 8, wherein the polymer is polypropylene.

10. A retainer clip for a conduit, comprising a base having a plane:
    a first body portion extending generally along a first side of the plane of the base;
    a second body portion extending generally along a second side of the plane;
    a hinge member connecting the first body portion and the second body portion, wherein the hinge member extends along the plane; and
    a locking section for releasably connecting the first body portion and the second body portion to define a passage for a conduit when the first and second body portions have been rotated about the hinge member into a closed position about the conduit;
    first and second manually engageable tabs at free ends respectively of the first and second body portions protruding outwardly for manual engagement enabling the first and second body portions to be pried apart to an open position for opening the conduit passage and releasing the conduit: and
    a flexible member having a first end connected to the first body portion and a second end connected to the second body portion and is disposed in the passage to engage and tightly surround and grip the conduit when the conduit is placed thereinto.

11. The retainer clip according to claim 10, wherein the passage is sized to retain a conduit disposed therein.

12. The retainer clip according to claim 11, wherein, when the conduit is disposed in the passage, the flexible member helically wraps around and clamps down on the conduit.

13. The retainer clip according to claim 12, wherein the flexible member restricts movement of the conduit in a direction parallel to a longitudinal length of the hinge member.

14. The retainer clip according to claim 10, wherein adhesive is disposed on bottom faces of the first and second body portions.

15. The retainer clip according to claim 1, wherein the first and second connector portions are identical to each other.

16. The retainer clip according to claim 1, wherein the first and second connector portions form a generally cylindrical conduit passage in the closed position.

17. The retainer clip according to claim 1, wherein the first and second free ends protrude outwardly for manual engagement enabling the first and second connector portions to be pried apart for opening the conduit passage.

18. The retainer clip according to claim 2, wherein, when the conduit is disposed in the passage, the flexible member helically wraps around the conduit and clamps down on the conduit and restricts movement of the conduit in a direction parallel to a longitudinal length of the hinge.

* * * * *